United States Patent [19]
Schrepp et al.

[11] Patent Number: 5,294,402
[45] Date of Patent: Mar. 15, 1994

[54] CHEMICAL SENSORS

[75] Inventors: Wolfgang Schrepp, Heidelberg; Ramesh C. Ahuja; Wolfgang Budach, both of Goettingen; Dietmar Moebius, Waake, all of Fed. Rep. of Germany

[73] Assignee: BASF Aktiengesellschaft, Ludwigshafen, Fed. Rep. of Germany

[21] Appl. No.: 904,629

[22] Filed: Jun. 26, 1992

[30] Foreign Application Priority Data

Jun. 28, 1991 [DE] Fed. Rep. of Germany ....... 4121426

[51] Int. Cl.$^5$ ............................................ G01N 21/17
[52] U.S. Cl. ....................................... 422/57; 422/52;
422/56; 422/82.05; 422/82.07; 422/82.09;
436/172
[58] Field of Search ................... 422/56, 52, 57, 82.04,
422/82.07, 82.05, 82.01, 82.09; 436/172

[56] References Cited

U.S. PATENT DOCUMENTS

| | | |
|---|---|---|
| 4,568,518 | 2/1986 | Wolfbeis et al. ............... 422/56 |
| 4,716,121 | 12/1987 | Block et al. .................... 422/57 |
| 4,954,318 | 9/1990 | Yafuso et al. ................... 422/59 |
| 4,965,087 | 10/1990 | Wolfbeis et al. ............... 436/172 |
| 4,999,306 | 3/1991 | Yafuso et al. .................. 436/68 |
| 5,006,716 | 4/1991 | Hall .............................. 436/172 |
| 5,030,516 | 7/1991 | Wehrmann et al. ............. 428/480 |
| 5,081,041 | 1/1992 | Yafuso et al. .................. 436/68 |
| 5,081,042 | 1/1992 | Yafuso et al. .................. 436/68 |
| 5,114,676 | 5/1992 | Leiner et al. .................. 422/82.07 |
| 5,132,095 | 7/1992 | Koshiishi et al. .............. 422/82.07 |

FOREIGN PATENT DOCUMENTS 150905 8/1985 European Pat. Off. .
3830325 3/1990 Fed. Rep. of Germany .

OTHER PUBLICATIONS

M. Aizawa et al. "Thin Solid Films" 160 1988), pp. 477–481 *An Optical Chemical Sensor using . . . Langmuir-Blodgett Film.*

M. Aizawa et al. "Thin Solid Films" 180(1989) pp. 227–233; *Molecular Film Techn. for Biosensors.*

"Nature" v. 320 Mar. 13, 1986, pp. 179–181 *Letters to Nature.*

Analyst, May 1988 v. 113 Optical Sensors, Part 23 by Schaffer, Wolfbeis, & Leitner, pp. 693–697.

Analytical Chimica Acta, 217 (1989) pp. 1–9; *A Calcium-Selective . . . Membrane Potential* by Schaffar & Wolfbeis.

Analyst; Apr. 1990, vol. 115 pp. 353–358 *Fibre Optic Sensor for the Detection . . . Energy Transfer* by Roe et al.

Polymer Surfaces & Interfaces; W. J. Feast & H. S. Munro 1987 Molecular Engineering using the Langmuir-Blodgett Techn. by M. C. Petty pp. 163–187.

"Thin Solid Films", 132(1985) pp. 135–151; *Penetration Controlled Reactions . . . Chain Surfactants* by Maoze Sagiv.

H. Vuhn et al. "Phys. Methods of Chemistry"; Teil III B, (1972) S. 577 pp. 600–628 Spectroscopy of Mon layer Assemblies.

D. Möbius: "Designed Monolayer Assemblies" Ber. Bunsenges Phys. Chem. 82, 848–858 (1978).

(List continued on next page.)

Primary Examiner—James C. Housel
Assistant Examiner—Harold Y. Pyon
Attorney, Agent, or Firm—Keil & Weinkauf

[57] ABSTRACT

A chemical sensor consists of
(a) a solid substrate,
(b) a layer (D) which is applied to the substrate and contains one or more fluorescent compounds and
(c) a layer (A) which is applied to the layer (D) and contains one or more coupling components. (K) which, as a result of reacting with the analyte, give rise to one or more specific absorption bands, some or all of which overlap in the spectrum with the emission of the fluorescent compound of layer (D).

12 Claims, 5 Drawing Sheets

OTHER PUBLICATIONS

F. Embs et al. "Adv. Mater" 3 (1991) No. 1 pp. 25–31 Preformed Polymers for Lagmuir . . . Concepts.

S. Misumi "Pure & Appl. Chem." v. 62, No. 3, pp. 493–498 (1990) Amine Selective Coloration with Chromoacerands.

I. O. Sutherland "Pure & Appl. Chem." vol. 62, No. 3, pp. 499–504 (1990) Cyclophanes as Synthetic Receptors.

S. Yoshida "Chem Lett.", pp. 243–246(1989) Ion Sensitive Tin Oxide Electrodes Carrying Amphiphillic Crown . . . Films.

J. Sondermann "Liebigs Ann. Chem." v. 749, pp. 183–197 (1971) Darstellung oberflächenaktiver . . . Ketten.

Th. Arndt et al. "Thin Solid Films"vol. 178(1989) pp. 319–326 Self–Assembled and Longmuir–Blodgett . . Study.

CHEMICAL SENSORS

BACKGROUND OF THE INVENTION

1. Field of the Invention

The present invention relates to a chemical sensor which consists of a solid substrate and discrete layers which are applied thereon and have different compositions, said sensor being suitable for detecting ions or organic molecules.

2. Description of the Related Art

Sensors based on fluorescent dyes have long been known. For example, M. Azzawa et al. (Thin Solid Films 160 (1988), 477) describe a sensor in which one or more layers of a fluorescent dye are brought into contact with the analyte to be investigated. As a result of interaction with one or more components of the analyte, a change occurs in the intensity of fluorescence. As a rule, fluorescent substances which exhibit a reduction in fluorescence, i.e. quenching, are used. A similar application in the area of biosensors is described by M. Azzawa et al. in Thin Solid Films 180 (1989), 227.

Sensors which are based on fluorescence transfer and in which the fluorescence of dye 1 is transferred to a second fluorescent dye are also known. These systems use a second fluorescent dye which, for example, may be bound to a component of the analyte (cf. for example European Patent 150 905). The detection of energy transfer in waveguide structures by means of evanescent waves has also been described (Nature 320 (1986), 179).

O. S. Wolfbeis et al. have described a number of sensors which utilize the quenching of fluorescence due to potential-sensitive dyes, the Langmuir-Blodgett method being used in some cases (Analyst 113 (1988), 693; Anal. Chim. Acta 217 (1989), 1).

J. N. Roe et al. (Analyst 115 (1990), 353) describe a fiber-optical sensor in which the fluorophore and the ionophore valinomycin, which is sensitive to potassium ions, were applied in an inhomogeneous polymer layer about 6 μm thick to the fibers.

The sensors described to date are either all based on direct quenching of the fluorescence by the analyte, are present together with an absorber in a polymer matrix or utilize potential-sensitive dyes.

The response times of such sensors are limited by the diffusion of the analyte in the sensor system, and a reference electrode which is intended to increase the selectivity is generally used. In many cases, dip coat layers which are relatively thick are used for this purpose.

SUMMARY OF THE INVENTION

It is an object of the present invention to provide a chemical sensor which has substantially shorter response times, can be produced reproducibly and in a relatively simple manner and can also be used at very high dilutions of the analyte ($10^{-10}$ to $10^{-6}$ molar).

We have found that this object is achieved, surprisingly, by the novel chemical sensor. The present invention relates to a chemical sensor consisting of (a) a solid substrate,
(b) a layer (D) which is applied to the substrate and contains one or more fluorescent compounds and
(c) a layer (A) which is applied to the layer (D) and contains one or more coupling components (K) which, as a result of reacting with the analyte, give rise to one or more specific absorption bands, some or all of which overlap in the spectrum with the emission of the fluorescent compound of layer (D).

In a possible further embodiment of the novel chemical sensor, an intermediate layer (Z) having a defined dipole moment, is applied between layer (D) and layer (A) to control the chemical equilibria in the adjacent layers, and such intermediate layers (Z) may consist, for example, of long-chain alcohols, carboxylic acids, carboxylic esters, amines or inert organic polymers. The layers applied to the solid substrate preferably have a total thickness of from 20 to 200 Å.

In other preferred embodiments of the novel chemical sensor, the solid substrate consists of quartz or glass and may be pretreated, and the coupling components (K) of layer (A) on the surface of the sensor are in direct contact with the solution of the analyte.

The distance between the chromophore of the donor layer (D) and the coupling components of the acceptor layer (A) preferably corresponds to the Förster radius.

Either the donor layer (D) may consist of the fluorescent compound or the fluorescent compound may be distributed or bound in a polymer or monomer matrix.

It is also preferable if J aggregates or disk aggregates are formed in layer (D).

The coupling component (K) of the acceptor layer (A) may be a compound capable of interacting with ions or organic molecules by a host/guest reaction, for example inclusion compounds in the case of clathrates or cryptands. Another possible embodiment of the acceptor layer would contain the coupling components (K) consisting of one or more complexing agents which are capable of reacting with ions, in particular heavy metal ions.

Layers (D) and (A) and, where relevant, (Z) can be applied to the solid substrate by various methods, for example by spin coating, by adsorption from solution, by the vapor deposition method and the self-assembly method and preferably by the Langmuir-Blodgett and-/or Langmuir-Schäfer method.

In the novel chemical sensor, a donor layer (D) which contains one or more suitable fluorescent dyes is thus present on a suitable solid substrate. An acceptor layer (A) on top contains a coupling component (K) which is capable of reacting with the analyte to be investigated or with a component thereof. This reaction results in the formation of an acceptor whose bands overlap in the spectrum with the emission of the fluorescent dye in the donor layer (D). Before the reaction, the absorption of coupling component (K) is relatively low and in the region of the emission of (D). The reaction with the analyte results in a compound which has a changed absorption spectrum which thus produces a change in the overlap with the donor fluorescence spectrum. This causes quenching of the donor fluorescence, which is readily detectable.

The donor layer (D) and the layer (A) which contains the coupling component (K) and which becomes the acceptor layer (A) *after* interacting with the analyte are preferably produced by the Langmuir-Blodgett or Langmuir-Schäfer method (the principle of which is described in, for example, W. J. Feast and H. S. Munro, Polymer Surfaces and Interfaces, J. Wiley & Sons, Chichester 1987, page 163 et seq.) or by chemisorption by the self-assembly method (cf. Thin Solid Films 132 (1985), 135). As is known to the skilled worker, the stated methods permit the production of very defined and ordered layers. The layer distances can be adjusted down to the Ångström unit range.

Compared with the sensors described to date, the novel chemical sensor permits the defined use of the Förster transfer (cf. Th. Förster, Fluorezenz Organischer Verbindungen, Vandenhoeck & Ruprecht, Göttingen (1950), pp. 67 to 86; H. Kuhn et al. in Weissberger and Rossiter (Eds.), Physical Methods of Chemistry, Part III B, Wiley, New York 1972, page 577 et seq.). The term Förster transfer is used when the fluorescence energy of the donor layer is transferred to the acceptor layer without radiation or by resonance. This energy transfer is very greatly dependent on the distance between the donor and the acceptor. According to Förster, the effectiveness of the energy transfer is described by a critical distance between the donor and the acceptor, $d_0$. This distance $d_0$ is as a rule from 20 to 100 Ångström units. As demonstrated in the work by H. Kuhn et al. cited above, the Langmuir-Blodgett method is very suitable for the production of molecular assemblies which are based on the Förster principle.

A great increase in the sensitivity and selectivity can be achieved by the principle of Förster transfer. This immediately becomes clear if monomolecular layers are considered by way of example. In general, a monomolecular dye layer absorbs a few percent of the incident light in the region of the absorption maximum. Accordingly, only a small fraction of the fluorescent light of a donor layer is absorbed by an acceptor layer over 100 Ångström units away. Below a certain distance, however, Förster energy transfer occurs: if the donor and acceptor layers are separated from one another by the Förster radius $d_0$ (Th. Förster, Fluoreszenz, Organischer Verbindungen, Vandenhoeck & Ruprecht, Göttingen (1950)), the intensity of fluorescence of the donor is quenched by about 50%. The corresponding energy is transferred without radiation or by resonance to the acceptor and is released by the latter in turn by emission or by nonradiant deactivation. The intensity of fluorescence of the donor exhibits S-shaped behavior as a function of the acceptor distance, the point of inflection corresponding to the Förster radius. If the distance is less than 20% of the Förster radius, the donor fluorescence is virtually completely quenched. For many dyes, the Förster radius is from 20 to 100 Ångström units. In the case of the dyes shown on pages 8 to 10, the radius is about 50 Ångström units. As a result of the overlap between the characteristic fluorescence of a donor dye and the characteristic absorption of an acceptor formed in the adjacent layer during the measurement (Förster energy transfer), and due to controlled layer build-up, high selectivity and sensitivity of the sensor are achieved.

Figure 1:
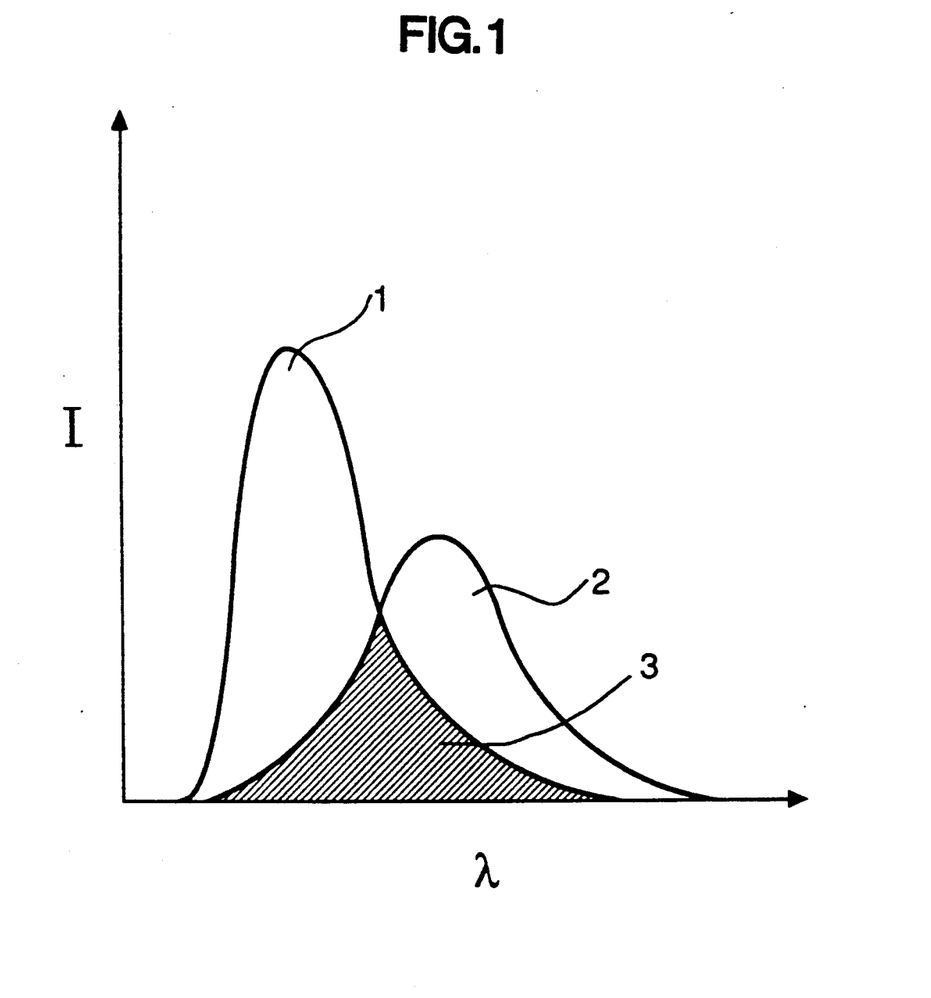
FIG. 1 shows the energy transfer on which the sensor is based;
1 = Donor fluorescence
2 = Acceptor absorption
3 = Spectral overlap.
Figure 2:
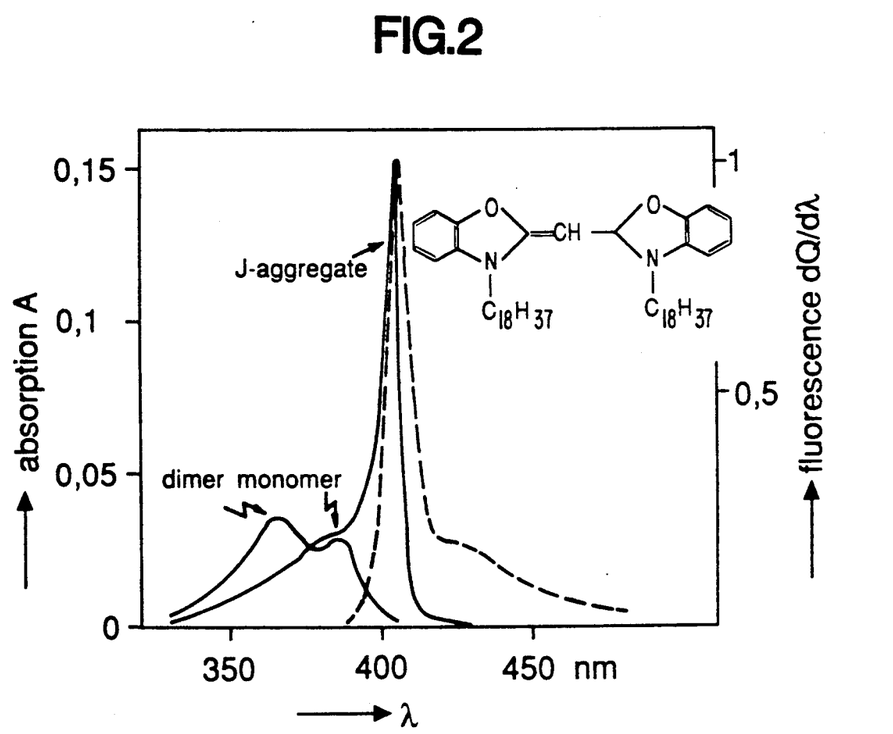
FIG. 2 shows a dye suitable for aggregate formation, together with the associated spectra.

A further increase in the effectiveness of the novel sensor principle is possible if, instead of normal fluorescent dyes, aggregates (e.g. J. or disk aggregates) are used in layer (D). Disk aggregates (cf. H. Kuhn et al.) result from specific aggregation of dyes and can be produced by the Langmuir-Blodgett method. They are distinguished by a very narrow-band fluorescence and can thus be very efficiently used on the basis of the novel sensor principle. They can produce an increase in sensitivity since complete spectral overlap with an acceptor band can occur more easily in the case of a narrow fluorescence band. Moreover, the selectivity of the sensor can also be increased in this manner since the formation of the acceptor from coupling component (K) and analyte may lead to different spectra for different analytes or different analyte components. By a suitable choice of the fluorescent dye or disk aggregate, a discrimination can be achieved here. FIG. 2 is a schematic illustration (from D. Möbius, Ber. Bunsenges. Phys. Chem. 82 (1978), 848).

Since the functional units of the novel sensor (donor molecules of layer (D) and coupling components (K)) are incorporated in separate layers, aggregation or orientation as well as the other film properties can be influenced and adapted to the requirements.

In the novel sensor, there are a number of obvious changes which however do not affect the principle. For example, it is possible for the donor layer and/or acceptor layer to each consist of one or more layers, for a plurality of fluorescence dyes and/or coupling components to be used, for intermediate layers to be applied (for example to improve the adhesion to the substrate or to adjust the distances between the donor layer and the acceptor layer) and for intermediate layers having a defined dipole moment to be employed for controlling the chemical equilibria in the adjacent layers.

The above embodiments give rise to a number of advantages of the novel sensor principle. The layer structure of the sensor permits optimal adaptation of the fluorophore and coupling component to the species to be detected. Particularly when the Langmuir-Blodgett method is used, the sensor can be produced in a very defined and reproducible manner. By utilizing Förster transfer, especially with the use of disk aggregates, it is possible to produce highly effective and selective sensors. A plurality of species can be detected simultaneously by a suitable combination of donor and acceptor components.

There are the following advantages over the sensors which contain the fluorophore and absorber component in one and the same layer: The distance which is decisive for Förster transfer can be established in a defined and reproducible manner. The spectroscopic advantages of disk aggregates (also referred to as J aggregates) can be made use of. It is known that both fluorophores and the acceptors can form relatively undefined aggregates and domains, so that it is not possible to utilize the full effectiveness when they are present in one layer, since only some of the existing systems are present at a defined distance. The bandwidth of possible donors and acceptors is limited in the event of the presence in one and the same layer, since it is necessary to find a solvent compatible with both components and a compatible matrix.

The novel sensor merely requires two main components (donor dye and coupling component), which are incorporated in separate, adjacent layers. Separation phenomena are thus avoided. The complex-forming hydrophilic coupling component (K) is in direct contact with the aqueous solution of the analyte. The acceptor complex thus obtained is formed at the solid/liquid interface. The speed of the sensor is thus dependent only on the type of chemical bond and on the geometry of the reaction vessel. There is thus no delay in the sensor response owing to the diffusion of the analyte through the sensor system.

In general, therefore, the analytical concept achieved with the novel sensor is flexible, has defined sensitivity, is selective, reproducible and rapid and, in terms of the principle, is very generally applicable.

Regarding the components and the production of the novel sensor, the following may be stated specifically.

For the sensor comprising a donor layer (D) applied to a solid substrate and a layer (A) which contains a coupling component (K) and which, after reaction with an analyte, becomes an acceptor layer, the following may be used as the solid substrate: glass, quartz, semiconductor materials, such as germanium, GaAs or silicon, Li niobate, zinc selenide, porcelain, metallic layers, optofibers, waveguide structures, plastics and specially pretreated substrates, for example water-repellant, plasma-treated or precoated substrates. Quartz and glass, which may have been rendered water-repellant, are preferred.

The layers are preferably produced by the Langmuir-Blodgett method. As is known to the skilled worker, this is a method for transferring monomolecular layers to solid substrates. The monomolecular layer is produced on the liquid surface (generally water) of a Langmuir trough by compression after the solutions of the substances to be applied to the substrate have been spread over the water surface. As a rule, these are amphiphilic substances. The monofilm is usually transferred to the substrate, which has generally been specially pretreated, by immersion and withdrawal through the film on the liquid surface using a film lift. The substrate may be dipped either at right angles to the liquid surface or at a certain angle (Langmuir-Blodgett method) or parallel to the liquid surface (horizontal dipping). If the substrate is brought into contact with the liquid surface at specific points or at an edge and then swivelled onto the surface, the term Langmuir-Schäfer method is used.

However, the layers can also be produced by other methods, but a deterioration in properties may have to be accepted. Thus, application of the layers is also possible, for example, by defined chemisorption processes (self-assembly). Here, generally organic compounds which have been modified to give long-chain ones are dissolved in relatively dilute form in more or less polar solvents. If a suitably pretreated substrate is then dipped into this solution, ordered chemisorption onto the substrate takes place. The layers may be highly ordered and multilayers can be produced. Other possible methods are, for example, plasma polymerization, spin coating, vapor deposition and physisorption.

In the production of the sensor, it is also possible to use different production processes for the individual layer systems. For example, the pretreatment of the substrate may be effected by chemisorption and the production of the active layers (D) and (A) by means of the Langmuir-Blodgett method.

Examples of fluorescent compounds in the donor layer (D) are the following fluorescent dyes where X and Y independently of one another are each O, S or Se and $R^1$, $R_2$ and $R_3$ independently of one another are each $C_1$-$C_{22}$-alkyl, where R is $C_{15}$-$C_{30}$-alkyl A further selection of suitable dyes appears, for example, in the abovementioned publication by H. Kuhn et al. If the donor layer is produced by the Langmuir-Blodgett method, the fluorescent dyes may be mixed in unmodified form into a matrix of substances suitable for the Langmuir-Blodgett method, for example long-chain fatty acids or modified polymers. The dyes may also be modified so that they are directly suitable for the Langmuir-Blodgett method, for example Direct binding of the fluorescent dyes to polymers is also possible, including binding to fluorescent dyes suitable for the Langmuir-Blodgett method (cf. for example F. Embs et al., Adv. Mat. 3 (1991), 25). Other suitable polymers are described in, for example, German Laid-Open Applications DOS 3,830,325 or DOS 3,830,862.

As already mentioned above, the specific aggregation of fluorescent dyes may lead to a substantial increase in fluorescence and hence to an increase in the sensitivity and selectivity of the sensor. FIG. 2 shows a dye which is suitable for aggregate formation, together with the associated spectrum. J or disk aggregates can be produced on the water surface of a Langmuir trough from a 1:1 mixture of N',N-dioctadecyloxacyanine perchlorate with hexadecane, dissolved in chloroform.

According to the invention, a layer (A) containing one or more coupling components (K) is applied to the donor layer (D): for the acceptor layer obtainable therefrom, it is decisive that a change in the absorption spectrum occurs.

Suitable substances having coupling components are compounds which are known to the skilled worker from analytical chemistry, are used for photometric purposes and, for example, form strongly colored compounds with a number of ions. Examples of these are i.e. dithiocarbamates which, for example, react with ions of Fe, Co, Cd or Hg, cuproins or bipyridyls which react with Cu ions, and dithiozones which, for example, react with Pb ions with formation of a strongly colored compound. These compounds, too, can be modified so that they are suitable for the Langmuir-Blodgett method or can be introduced into a mixed layer. The latter may also be possible without special modification of the starting substance.

From host/guest chemistry (cf. for example Vögtle, Supramolekulare Chemie, Teubner Verlag, Stuttgart (1990)), it is known that, for example, a number of complexes and inclusion compounds are formed between a cationic or neutral guest molecule, for example crown molecules, cryptands, cyclodextrins, etc. with ions of an analyte, and frequently considerable changes in the absorption spectrum may occur. An example of this is the reaction of the compound n = 1, 2 with Ba ions, the colour changing from yellowish orange to bluish violet. A further example is the reaction of with Sr ions. The inclusion of a plurality of ions in such a cage compound is also possible (cf. F. Vögtle). With the aid of host/guest chemistry, however, it is possible to detect, for example, not only metal ions but also organic molecules including biomolecules. For example, S. Misumi, Pure Appl. Chem. 62(3) (1990), 493 states that, in the reaction of azobenzene-containing crown molecules with amines a substantial change in the absorption spectrum occurs. Cyclophanes, too, are suitable for detecting organic molecules (I. O. Sutherland, Pure Appl. Chem. 62(3) (1990), 499). Thus, bis-Zn porphyrin is a selective host for 4,4-bipyridyl Thus, such molecular systems can also be used as an acceptor layer for the purposes of the present invention. On this basis, detection of biomolecules or drug metabolites is also possible.

Crown ethers can be modified so that they can also be transferred by the Langmuir-Blodgett method (cf. S. Yoshida et al. , Chem. Lett. 2 (1989), 243); an example is octadecyloxymethyl 18-crown-6.

The selectivity of the novel sensor can be influenced not only by the skillful choice of the donor and the acceptor layer; the selectivity can be increased also by pretreatment of the analyte by pH adjustment and/or complexing, as is known to the skilled worker from photometric detection reactions of analytical chemistry.

When suitable coupling components (K) are used, for example in conjunction with host/guest chemistry, it is also possible to produce reversible sensors. The use, described above, of photometric reagents would, as a rule, lead only to single-use sensors since the coupling reaction is irreversible.

The sensor layer or the coupling component can be reactivated by treatment with an aqueous solution of a more strongly complexing molecule (e.g. EDTA), so that the sensor can be used in a reversible manner.

EXAMPLE

The reagents arachidic acid ($=C_{20}$), methyl arachidate ($=$ AME), $CuCl_2$ and $CdCl_2$ used were each analytical grade materials from Merck, Darmstadt.

The fluorescent dye

N′,N-Dioctadecyloxacyanine perchlorate (S9) was synthesized by a method due to Sondermann (Liebigs Ann. Chem. 749 (1971), 183). The spreading solvent used was chloroform (Baker Chemicals, spectroscopic grade), stabilized with 1% by volume of ethanol. Dioctadecyldithiocarbamate was synthesized according to Th. Arndt et al., Thin Solid Films 178 (1989), 319, and was dissolved freshly in chloroform before the experiment. Deionized and purified water from a Milli-Q system (Millipore) was used as the subphase.

Production of the Langmuir-Blodgett Layers a) Donor layer (D)

Quartz lamellae (38 mm × 12 mm × 1 mm) were rendered water-repellant with dimethyldichlorosilane and then used as the solid substrate. First, a layer of cadmium arachidate was applied at 30 mN/m. A monolayer which was produced on the subphase containing cadmium$^{2+}$ ions and contained the fluorescent dye (S9) was then transferred at the same surface pressure (S9:AME:C$_{20}$ = 1:2:18).

b) Acceptor layer

Figure 3:
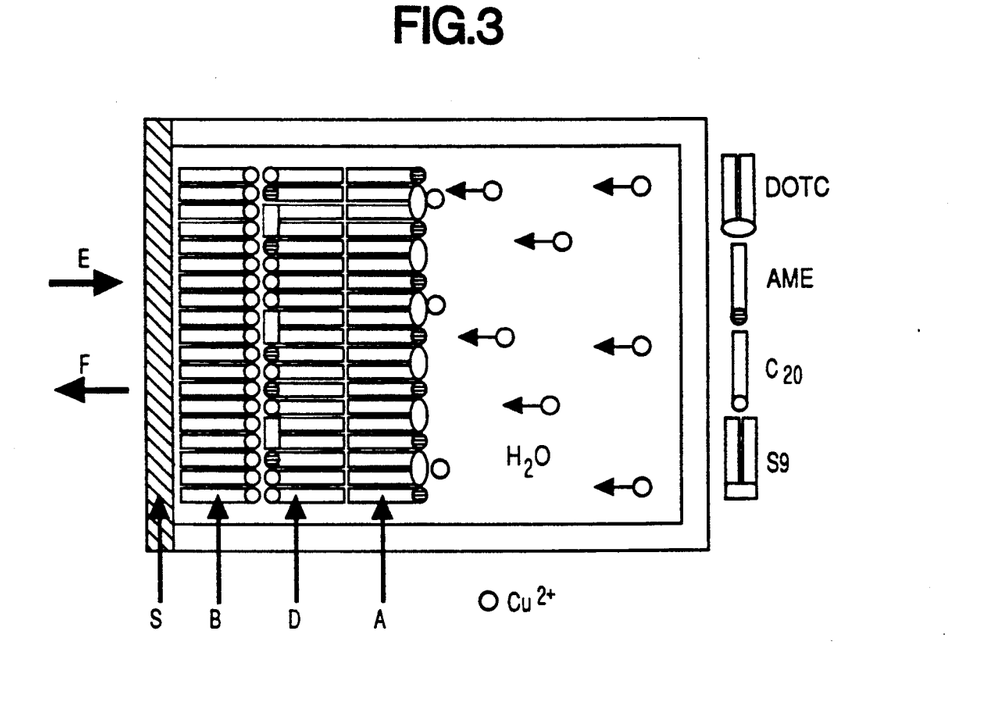
FIG. 3 schematically shows the structure of a sensor; in this figure,
S = Solid substrate
B = Pretreatment layer of arachidic acid (C20)
D = Layer (D) containing the fluorescent dye (S9) (S9:AME:C20 = 1:2:18)
A = Layer (A) containing the coupling component (K)
E = Excitation light (366 nm)
F = Fluorescent light
DOTC = Dioctadecyldithiocarbamate
AME = Methyl arachidate
C$_{20}$ = Arachidic acid
S9 = N′,N-Dioctadecyloxacyanine perchlorate.

Layer (A) was transferred as a 1:1 mixture of octadecyldithiocarbamate (=DOTC) and AME at 20 mN/m from an aqueous subphase to half the quartz lamellae covered with layer (D), DOTC containing the coupling component (K) for the novel sensor. The other half of the substrate was coated with pure AME, as a reference. The coated substrate was stored under water and served as the window of a small cell (38 mm × 12 mm × 8 mm). The Langmuir-Blodgett film is thus in contact with the aqueous phase in the cell (cf. FIG. 3), which can be exchanged for the ion-containing solution.

As a result of reaction with the analyte to be investigated, in this case a solution containing Cu$^{2+}$ ions, a change occurs in the absorption spectrum and layer (A) becomes the acceptor layer in terms of the Förster transfer.

Fluorescence Spectroscopy and Detection of the Sensor Effect

Figure 4:
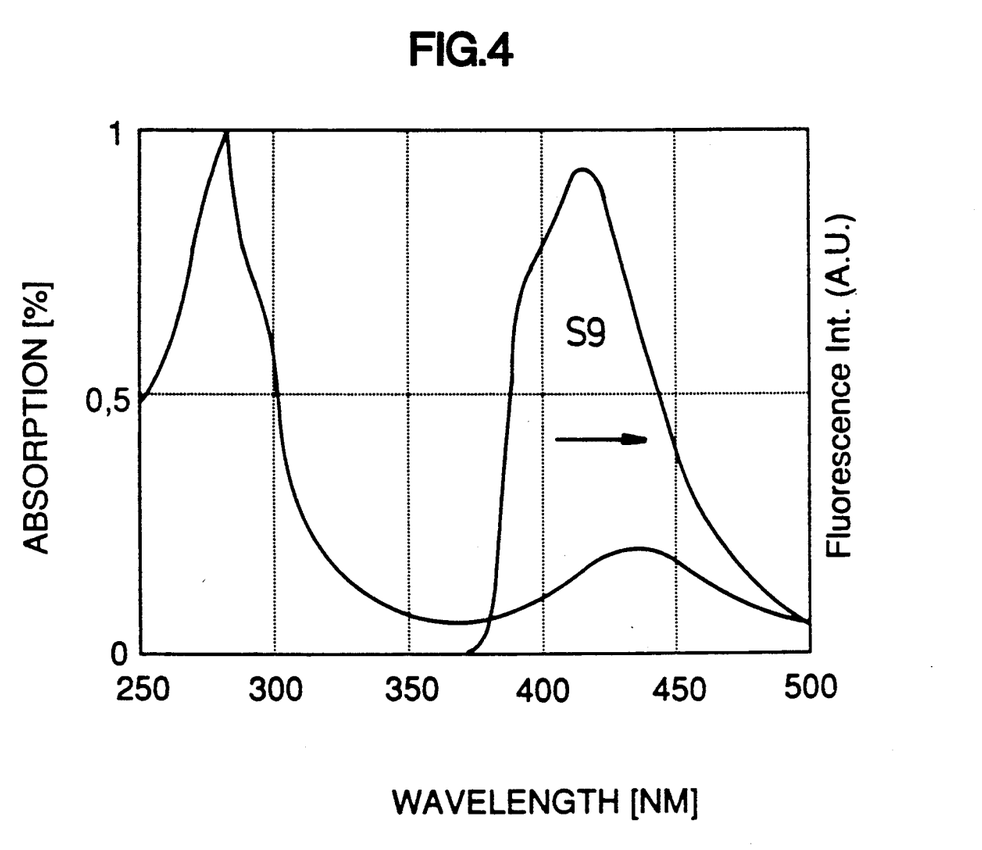
FIG. 4 shows the overlap of the absorption spectrum of the DOTC/Cu complex with the fluorescence spectrum of the donor dye S9.
Figure 5:
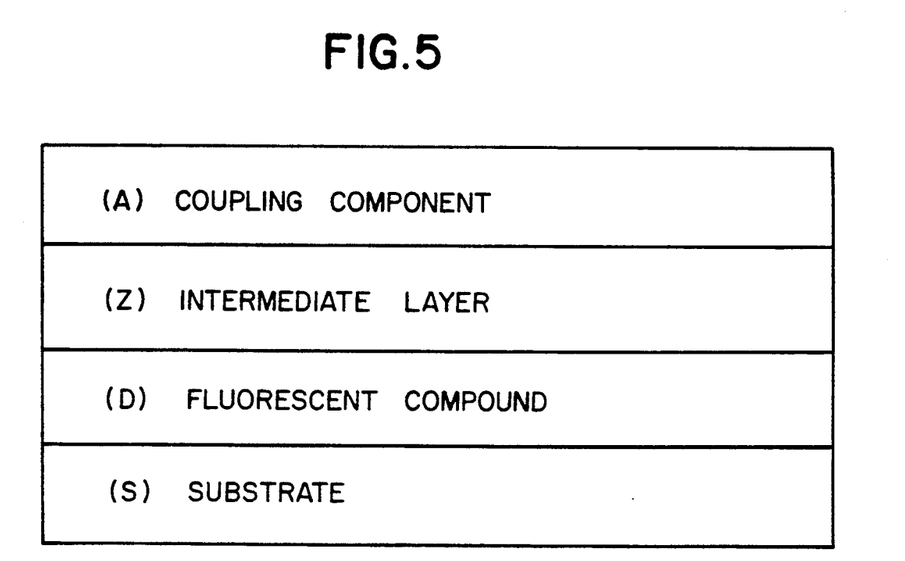
FIG. 5 shows a structure of a sensor containing layers
S = solid substrate,
D = donor layer containing a fluorescent dye,
Z = an intermediate layer having a defined dipole moment, and
A = a layer containing the coupling component (K).

A mercury vapor lamp was used as an excitation source for the fluorescence measurements. The donor molecules were excited at 366 nm and the emission was detected at 420 nm. The intensity of fluorescence decreases as the surface density of the resultant DOTC-copper complexes increases. In the case of a Cu$^{2+}$ concentration of more than $10^{-2}$M, about 70% quenching of the initial fluorescence is observed. The fluorescence of the donor is shown in FIG. 4. No effect on the reference half is observed, i.e. quenching of the fluorescence by the copper ion alone does not take place. The reaction with the coupling component is necessary for the sensor effect. Investigations show that the sensor in the present configuration operates in the concentrate on range from $10^{-9}$ to $10^{-2}$ Mol.

In the example chosen, the distance between the donor dye and the acceptor, which is formed by interaction of the coupling component with the analyte, is about 5 nm, which corresponds roughly to the critical Förster radius. The response times are less than 10 seconds and are limited primarily by the cell geometry.

We claim:

1. A chemical sensor to be used in a solvent containing an analyte consisting of
   (a) a solid substrate,
   (b) a layer (D) which is applied to the substrate and consists essentially of one or more fluorescent compounds and
   (c) a layer (A) which is applied to the layer (D) and consists essentially of one or more coupling components (K) which, as a result of reacting with the analyte, give rise to one or more specific absorption bands, some or all of which overlap in the spectrum with the emission of the fluorescent compound of layer (D).

2. A chemical sensor as claimed in claim 1, wherein the layers applied to the solid substrate have a total thickness of from 20 to 200 Å.

3. A chemical sensor as claimed in claim 1, wherein the solid substrate consists of quartz or glass and may be pretreated.

4. A chemical sensor as claimed in claim 1, wherein the coupling components (K) of layer (A) on the surface of the sensor are in direct contact with the solution of the analyte.

5. A chemical sensor as claimed in claim 1, wherein the distance between the chromophore of layer (D) and the coupling component of layer (A) corresponds to the Förster radius.

6. A chemical sensor as claimed in claim 1, wherein the fluorescent compound of layer (D) is present, distributed or bound in a polymer or monomer matrix.

7. A chemical sensor as claimed in claim 1, wherein J or disk aggregates are formed in layer (D).

8. A chemical sensor as claimed in claim 1, wherein the coupling component (K) of layer (A) is a compound which is capable of interacting with ions or organic molecules by a host/guest reaction.

9. A chemical sensor as claimed in claim 1, wherein the coupling component (K) of layer (A) consists of one or more complexing agents which react with ions.

10. A chemical sensor as claimed in claim 1, wherein layers (D) and (A) have been obtained by the Langmuir-Blodgett method.

11. A chemical sensor to be used in a solvent containing an analyte, consisting of
  (a) a solid substrate,
  (b) a layer (D) applied to the substrate and consisting essentially of at least one fluorescent compound,
  (c) a layer (Z) having a defined dipole moment applied to layer (D), and
  (d) a layer (A) applied to layer (Z) containing at least one coupling components (K) which, as a result of reacting with the analyte, gives rise to one or more specific absorption bands, at least one of which overlaps in the spectrum with the emission of the fluorescent compound of layer (D), the intermediate layer (Z) between layers (D) and (A) controlling the chemical equilibria of layers (D) and (A).

12. A chemical sensor as claimed in claim 11, wherein layers (D), (A), and (Z) have been obtained by the Langmuir-Blodgett method.

* * * * *